United States Patent [19]

Kaprelian

[11] Patent Number: 5,395,318

[45] Date of Patent: Mar. 7, 1995

[54] METHOD AND APPARATUS FOR WOUND TREATMENT

[76] Inventor: Edward K. Kaprelian, 15 Lowery La., Mendham, N.J. 07945

[21] Appl. No.: 185,044

[22] Filed: Jan. 24, 1994

[51] Int. Cl.[6] .................. A61M 31/00; A61M 37/00; A61M 35/00

[52] U.S. Cl. ........................ 604/56; 604/87; 604/265; 602/43; 602/46

[58] Field of Search .................. 602/41–43, 602/46, 904; 604/49, 54, 56, 58, 59, 82–88, 92, 244, 265

[56] References Cited

U.S. PATENT DOCUMENTS

| | | | |
|---|---|---|---|
| 2,731,965 | 1/1956 | Haralson, Jr. | 604/87 X |
| 3,648,695 | 3/1972 | Bowen | 128/225 |
| 3,667,652 | 6/1972 | Morane et al. | 604/56 X |
| 3,759,259 | 9/1973 | Truhan | 401/132 X |
| 3,955,572 | 5/1976 | Sunnen et al. | 604/131 X |
| 4,464,174 | 8/1984 | Ennis | 604/90 |
| 4,551,135 | 11/1985 | Gorman et al. | 604/82 |
| 4,568,331 | 2/1986 | Fischer et al. | 604/56 |
| 4,982,875 | 1/1991 | Pozzi et al. | 222/83 |
| 5,065,752 | 11/1991 | Sessions et al. | 602/46 |
| 5,089,606 | 2/1992 | Cole et al. | 536/54 |

FOREIGN PATENT DOCUMENTS 4119140  12/1992  Germany ........................... 602/46

Primary Examiner—John D. Yasko
Assistant Examiner—Alan J. Cermak

[57] ABSTRACT

In a wound treatment method and apparatus a multiplicity of separately packaged doses of antibiotics, coagulants, anesthetic agents, and similar medicaments are introduced into a wound by a foaming carrier which acts as a mixing and transport medium and also functions as a plug to retain the medication in the wound and to prevent the entry of contaminents and bacteria. The medication is introduced into the would site by means of a foamable carrier which entrains the medication during it travel through a medication cell.

17 Claims, 2 Drawing Sheets

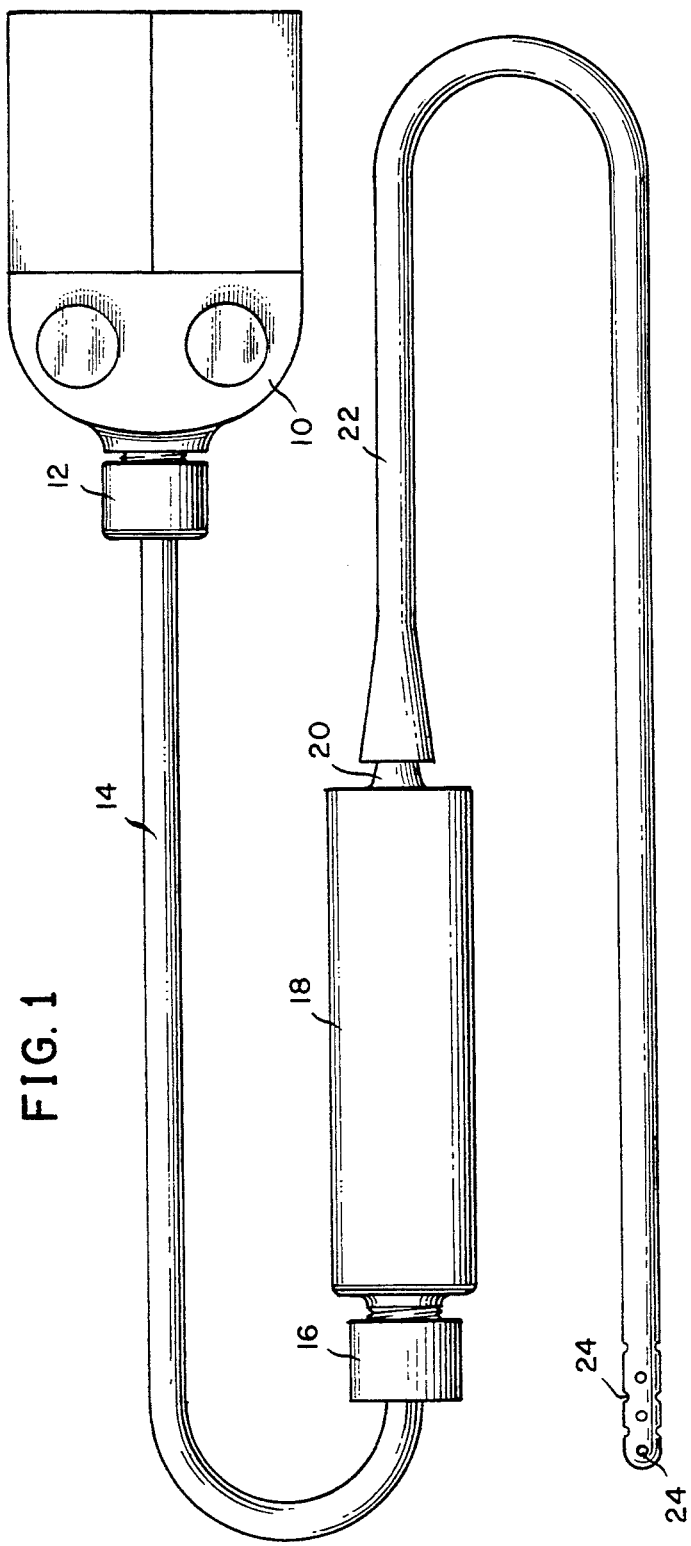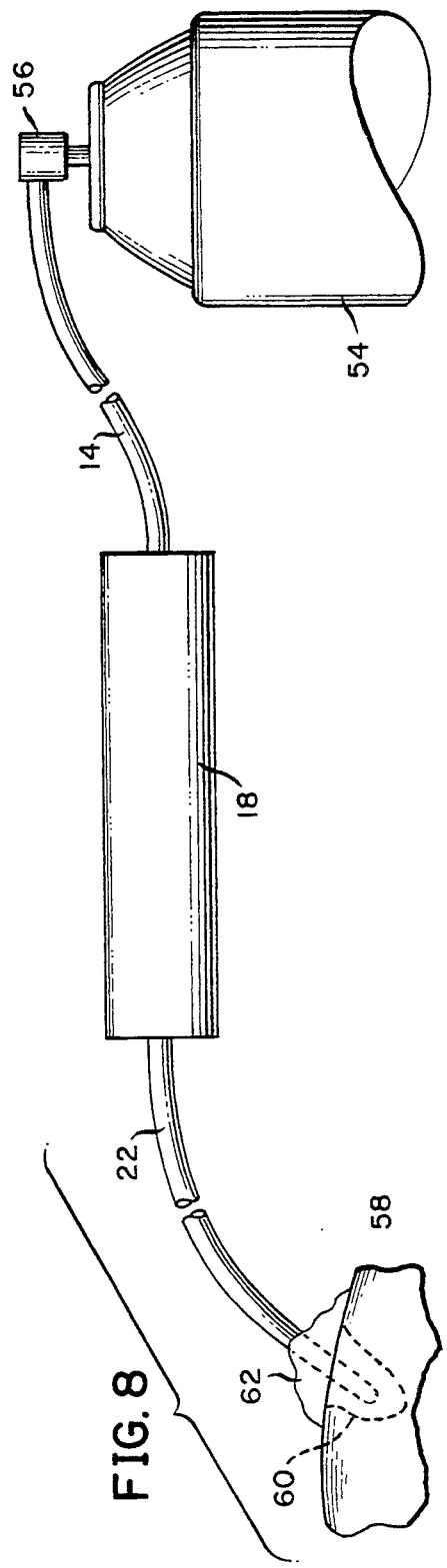

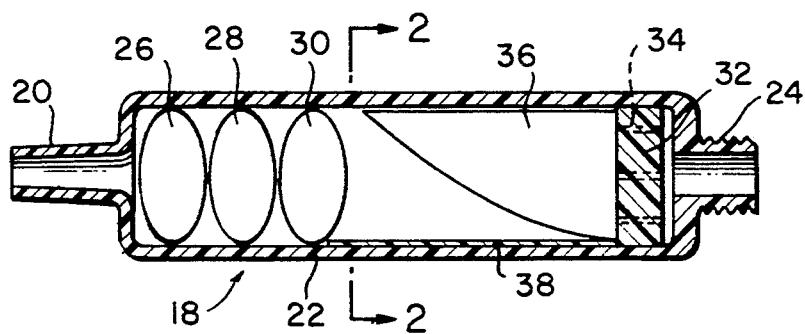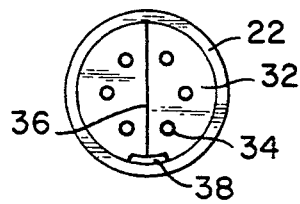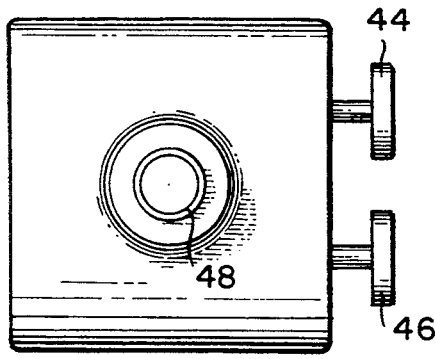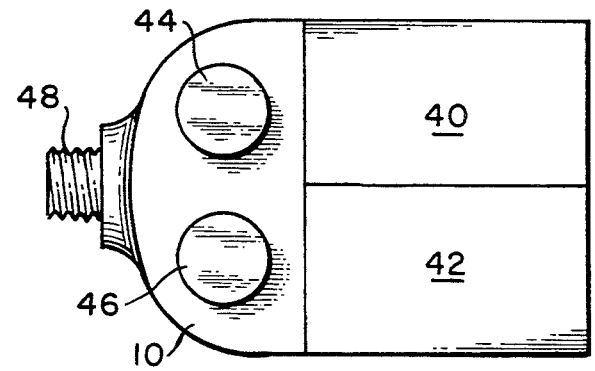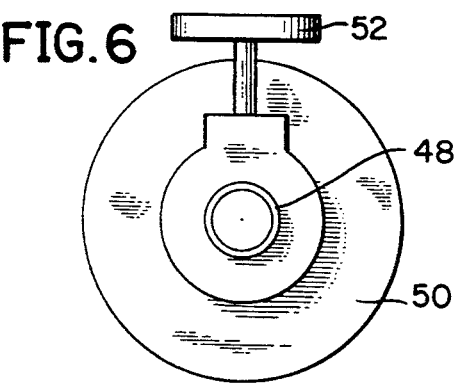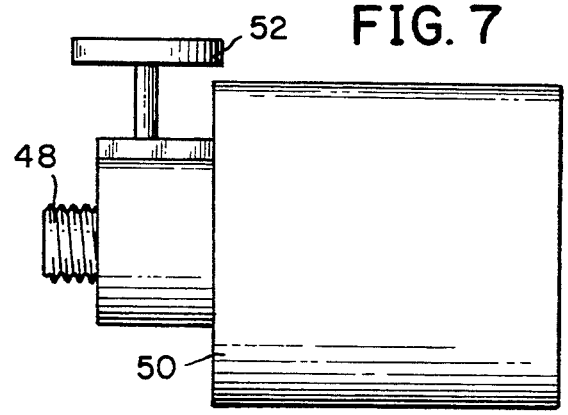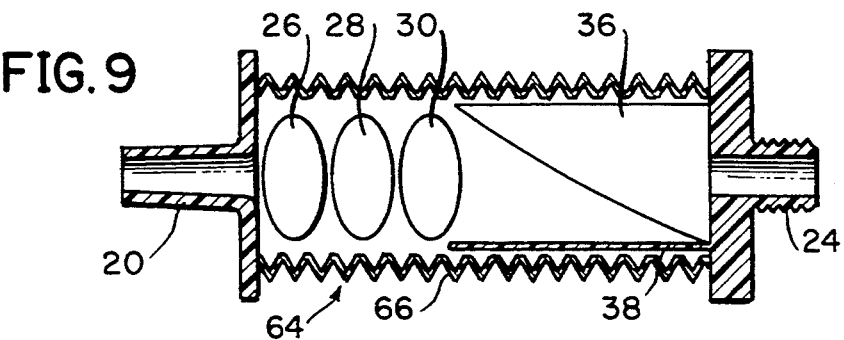

METHOD AND APPARATUS FOR WOUND TREATMENT

BACKGROUND OF THE INVENTION

1. Field of the Invention

This invention relates to a method and apparatus for the emergency treatment of wounds particularly those which are deep, or the path of which is difficult to ascertain.

In all wounds, but particularly those of the chest and abdomen it is essential, at the earliest time, that bleeding be stopped, an antibiotic, and an anesthetic agent be applied and the wound opening protected from a medically hostile environment. At present such procedures are taken separately and in many cases ineffectively; the medication fails to reach the deeper portion of the wound, the medication leaks from the wound, or the wound is not adequately protected from subsequent sources of bacteria and contaminents from the surroundings.

2. Prior Art

Syringes and applicators have been employed in the past for applying medication, including some which employed hydraulic pressure to deliver the medicament to the desired site.

One such device is the syringe shown in U.S. Pat. No. 4,551,135. Here two components of a plasticizable mixture are combined, one component having been stored within the barrel and a second component within a cylinder and piston arrangement. When the piston is moved the second component is pushed into the barrel, mixed with the first component and extruded to the target site.

U.S. Pat. No. 3,759,259 shows a two chamber medicator, one of which carries a wad of cotton or similar material and the second of which contains a fluid medicament. The two chambers are separated by a frangible seal which when broken allows the medicament to flow into the wad when the flexible wall of the second chamber is squeezed.

SUMMARY OF THE INVENTION

An object of this invention is to provide immediate and effective treatment for wounds, particularly those of the body-penetrating kind, using multiple medicaments. These medicaments, applied simultaneously, will act to stop bleeding, reduce pain and reduce the possibility of infection.

Another object of the invention is to provide a protective seal at the wound to prevent unwanted entry of dangerous substances in the adjacent environment.

Another object is to provide an easily operated device for achieving the objectives noted above.

Still another objective is to avoid mixing different medicaments prior the time of use.

The apparatus consists of a medicament chamber, a source of foamable material and a delivery tube for directing the mixture of medicaments and foam to and into the wound. Within the medicament chamber are several individual sealed packets of different medicaments. Also within the chamber is a piston-activated knife which acts to puncture said packets when advanced by pressure from the foamable material which subsequently mixes with the medicaments and drives, under pressure, the resulting mixture of foam and medicaments through the delivery tube to the wound site.

BRIEF DESCRIPTION OF THE DRAWINGS

FIG. 1 shows all the elements of the invention connected together for operation.

FIG. 2 shows a cross-sectional view of a preferred form of the medicator chamber.

FIG. 3 shows a view, along 3—3 of FIG. 2 of the piston and knife.

FIG. 4 shows a front view of a two cell foam-generating unit.

FIG. 5 shows the side view of the foam generating unit of FIG. 4.

FIG. 6 shows a front view of a single cell foam making unit of FIG. 6.

FIG. 7 shows the side-view of the single cell foam making unit of FIG. 6.

FIG. 8 shows an alternate source of foam material.

FIG. 9 shows a modified form of the medicator chamber.

DESCRIPTION OF THE PREFERRED EMBODIMENTS

FIG. 1 shows the elements of the invention connected together ready for use. These include foam-making unit 10 connected through coupling 12 to a flexible tube 14 connected in turn via coupling 16 to medicator chamber 18 which, via a Luer or similar taper joint 20, connects to flexible tube 22 provided at its far end a series of holes 24.

The medicator chamber 18 is preferably cylindrical in cross section and carries the tapered joint 20 at one end for attachment to tube 22 and a threaded extension 23 at the other end for accepting coupling 16 of tube 14.

Chamber 22 can be made of any of polypropylene, high density polyethylene or other flexible material compatible with the medicament.

Within the chamber 22 are several medicament containing capsules or pods 26, 28 and 30. These can take any other convenient form such as edge-sealed plastic packets. At the end of the chamber opposite the capsules is a piston 32 made of the same material as the cylinder and carrying a number of holes 34. The holes permit passage of foam without affecting the pushing power of the piston.

Attached to the piston and pointed toward the capsules is a curved knife 36 of stainless steel, hard thermoplastic or other suitable material. Carried by the piston just below the knife is a travel stop 38 which controls the maximum distance the knife can travel. Details of the piston and knife are shown in FIG. 3.

FIGS. 4 and 5 show the exterior of a two-cell foam generator which carries under pressure the liquid foam base material in a chamber 40 and the gaseous or liquid blowing agent also under pressure in chamber 42. Valves 44 and 46 control the mixing of the two substances prior to their exit through threaded extension 48 which connects with coupling 12. Here, the foam base material may be a water-absorptive polyurethane polymer with a small amount of isocyanate carried within chamber 40 and the blowing agent may be nitrogen or carbon dioxide carried under pressure within chamber 42. The resulting foam can have a consistency ranging from soft to semi-rigid. Numerous other systems based on polymers could be employed.

FIGS. 6 and 7 show the exterior of a single cell foam generator 50 within the body of which is carried under pressure the liquid foam base together with the gaseous or liquid blowing agent. Here, the foam base may be cellulose nitrate dissolved in amylacetate and acetone combined with carbon dioxide, nitrogen or nitrous oxide under pressure. Another combination for foam is a film forming fluoroprotein in aqueous solution pressurized with compressed air. Other foam making combinations with suitable properties may also be used. Some of the foams produced in FIGS. 4 to 7 are cohesive in nature, thereby permitting subsequent removal of the foam structure in one or a few pieces.

FIG. 8 shows an alternative source of foam which is not cohesive, but will function similarly to the sources in FIGS. 4 to 7 except for the removal stage. Container 54 provided with a push valve 56 contains whipping cream, shaving cream or other innocuous, readily available, foamable materials. The foam travels through tube 14, medicator chamber 18 and tube 22. The foam exits through holes 24 in tube 22 such as is shown in FIG. 1, and enters wound opening 60 in body 58 where it forms a protective mound 62. When operated similarly to the foam sources of FIGS. 4 to 7, these sources operate the knife, open the medicament containers and deliver the mixture to the wound site. Subsequent removal from the wound is accomplished by rinsing with water containing an antiseptic. In some instances the foam may be tinted with a contrasting color such as green or blue to readily recognize its presence on the tissue. The addition of radiopaque material such as barium sulfate to the foam of FIGS. 4 to 7 may be useful in some applications.

FIG. 9 shows a modification 64 of the medicament chamber of FIG. 2. Here, the body of the chamber is not a solid piece as in FIG. 2 but a flexible bellows 66 formed of any suitable thermoplastic material. In this simplified modification, the knife 36 is stationarily fixed to one end of the chamber opposite the pods 26, 28 and 30. In use, the two ends of the chamber are pressed together, compressing the bellows wall 66 and rupturing the pods in a manner similar to that shown in FIG. 2.

Many substances are suitable for use in the pods. Morphine, and other compounds such as oxycodone hydrochloride, meperidine hydrochloride and propoxyphene napsylate are useful ingredients in an anesthetic or anti-pain pod, staphylcoagulase or epinephrine are suitable in the clotting pod while any of the broad spectrum antibiotics such as ciprofloxicin hydrochloride are good choices for in the anti-infection pod.

I claim:

1. A device for delivering medication to a wound site comprising a source of foam under pressure, a medicament chamber containing a plurality of medicaments in individual packets conduit, means for delivering foam from the foam source to the chamber, means for rupturing the packets and conduit means for delivering the resultant mixture of medicament and foam to a wound.

2. The device of claim 1 wherein the means for rupturing the packets is a movable knife carried within the chamber.

3. The device of claim 2 including a piston connected to said moveable knife for moving said knife.

4. The device of claim 3 wherein pressured foam from the foam source delivered to the chamber acts on one side of the piston to move the piston.

5. The device of claim 3 wherein the piston is provided with perforations.

6. The device of claim 3 wherein the piston is provided with stop means to limit travel of the piston.

7. The device of claim 1 wherein the medicament chamber is made in the form of a compressible bellows and the means for rupturing the packets is a fixed knife in said chamber which upon compression of the bellows wall drives the packets into the knife.

8. A device for delivering medication to a wound comprising a source of foam under pressure, a medicament chamber, a first hose connecting said source of foam to said medicament chamber to provide foam thereto under pressure, two or more rupturable pods within the chamber each containing a medicament, puncturing means within said chamber activated by said pressurized foam to rupture said pods and a second hose connected to said chamber to deliver the resulting mixture of foam and medicaments to a wound site.

9. The device of claim 8 wherein said first and second hoses are disconnectibis from said source of foam and said medicament chamber, and said second hose is disconnectible from said medicament chamber.

10. The device of claim 9 wherein the end of said second hose is provided with perforations.

11. A wound treatment method for delivering medicaments to a wound site comprising delivering foam under pressure to a plurality of medicaments, mixing said foam and said medicaments and delivering the resultant flowable mixture to a wound.

12. The wound treatment method of claim 11 wherein the medicaments are held in unmixed state prior to activation by the delivery of the foam.

13. The wound treatment method of claim 11 wherein the medicaments include two or more from the group consisting of coagulants, antibiotics, and anesthetics.

14. The wound treatment method of claim 13 wherein the coagulants are selected from the group consisting of staphylcoagulate and epinephrine.

15. The wound treatment method of claim 13 wherein the medicaments include cyproflexicin hydrochloride.

16. The wound treatment method of claim 13 wherein the medicaments include anesthetic agents selected from the group consisting of morphine, meperidine oxyconone and propoxyphene.

17. In a wound treatment method for substantially simultaneously delivering two or more medicaments to a wound or similar site, improvement comprising the steps of activating a source of foam under pressure, directing the source of foam to a station carrying several individual stores of medicament, releasing the medicament from the stores as a result of pressure action by the foam, mixing the foam and the medication and delivering the resulting mixture of foam and medications to the wound site.

* * * * *